US008722360B2

(12) United States Patent
Aymerich et al.

(10) Patent No.: US 8,722,360 B2
(45) Date of Patent: May 13, 2014

(54) METHOD FOR PRODUCING A FERMENTATION PRODUCT USING A GENETICALLY MODIFIED MICROORGANISM WITH A MUTATION TO RELIEVE CARBON CATABOLITE REPRESSION

(75) Inventors: Stephane Aymerich, Versailles (FR); Hans-Peter Hohmann, Loerrach (DE); Uwe Sauer, Zürich (CH)

(73) Assignees: DSM IP Assets B.V., Heerlen (NL); Institute National de la Recherche Agronomique, Paris (FR)

( * ) Notice: Subject to any disclaimer, the term of this patent is extended or adjusted under 35 U.S.C. 154(b) by 1042 days.

(21) Appl. No.: 11/794,057

(22) PCT Filed: Dec. 22, 2005

(86) PCT No.: PCT/EP2005/013888
§ 371 (c)(1),
(2), (4) Date: May 29, 2008

(87) PCT Pub. No.: WO2006/066925
PCT Pub. Date: Jun. 29, 2006

(65) Prior Publication Data
US 2008/0311620 A1     Dec. 18, 2008

(30) Foreign Application Priority Data

Dec. 22, 2004   (EP) ..................................... 04030489

(51) Int. Cl.
*C12P 25/00*   (2006.01)
(52) U.S. Cl.
USPC ........................................................... 435/66
(58) Field of Classification Search
None
See application file for complete search history.

(56) References Cited

U.S. PATENT DOCUMENTS 5,684,144 A * 11/1997 Romeo ......................... 536/23.7
5,837,528 A * 11/1998 Perkins et al. ........... 435/252.31
2004/0091976 A1 * 5/2004 Deng et al. ...................... 435/84

OTHER PUBLICATIONS

Tännler et al., "Screening of *Bacillus subtilis* transposon mutants with altered riboflavin production", Metabolic Engineer. 10:216-226, 2008.*
Rahner et al., Deregulation of gluconeogenic structural genes by variants of the transcriptional activator Cat8p of the yeast *Saccharomyces cerevisiae* Mol. Microbiol. 34:146-156, 1999.*
Blencke et al., Metabolic Engineering 5:133-149, 2003.*
Grosskopf, Int'l Search Report for PCT/EP2005/013888, three pages, mailed Jun. 9, 2006.
Grosskopf, Written Opinion for PCT/EP2005/013888, seven pages, mailed Jun. 9, 2006.
Database UniProt [Online], "YqzB protein" retrieved from EBI accession No. UNIPROT: O34994, database accession No. O34994, Jan. 1, 1998.
Database UniProt [Online], "Conserved protein YqzB" retrieved from EBI accession No. UNIPROT: Q62SN5, database accession No. Q62SN5, Oct. 25, 2004.
Database UniProt [Online], "YqzB" retrieved from EBI accession No. UNIPROT: Q65H77, database accession No. Q65H77, Oct. 25, 2004.
Database UniProt [Online], "CBS domain protein" retrieved from EBI accession No. UNIPROT: Q81LU0, database accession No. Q81LU0, Jun. 1, 2003.
Database UniProt [Online], "BH1372 protein" retrieved from EBI accession No. UNIPROT: Q9KD47, database accession No. Q9KD47, Oct. 1, 2000.
Moreno et al., "Catabolite repression mediated by the CcpA protein in *Bacillus subtilis*: Novel modes of regulation revealed by whole-genome analyses" Molecular Microbiology, vol. 39, No. 5, pp. 1366-1381, Mar. 2001.
Servant et al., "CcpN (YqzB), a novel regulator for CcpA-independent catabolite repression of *Bacillus subtilis* gluconeogenic genes" Molecular Microbiology, vol. 55, No. 5, pp. 1435-1451, Mar. 2005.
Licht et al., "Implications of CcpN in the regulation of a novel untranslated RNA (SR1) in *Bacillus subtilis*" Molecular Microbiology, vol. 58, No. 1, pp. 189-206, Oct. 2005.

* cited by examiner

*Primary Examiner* — David J Steadman
(74) *Attorney, Agent, or Firm* — Nixon & Vanderhye P.C.

(57) ABSTRACT

The present invention is directed to novel genes mediating the carbon catabolite repression (CCR) of gluconeogenic genes. Furthermore, the polypeptides encoded by said genes as well as the use of said genes in a process for the production of a target fermentation product is provided. Processes for generating such microorganisms are also provided by the present invention. The invention is also related to a genetically engineered microorganism and its use for the production of a target fermentation product, wherein the gluconeogenic genes are relieved from CCR within said microorganism.

6 Claims, No Drawings

METHOD FOR PRODUCING A FERMENTATION PRODUCT USING A GENETICALLY MODIFIED MICROORGANISM WITH A MUTATION TO RELIEVE CARBON CATABOLITE REPRESSION

This application is a U.S. national stage of International Patent Application No. PCT/EP2005/013888, filed 22 Dec. 2005, which designated the U.S. and claims priority benefit of EP 04030489.1, filed 22 Dec. 2004; the entire contents of each of which are hereby incorporated by reference.

The present invention relates to novel nucleotide sequences, transformed microorganisms, and the use of said nucleotide sequences for the preparation of a target fermentation product. Processes for generating such microorganisms are also provided by the present invention.

More particularly, the present invention relates to novel genes, i.e. yqzB and yqfL, (URL: genolist-dot-pasteur-dot-fr/SubtiList) involved in the expression of gluconeogenic genes, e.g. phosphoenolpyruvate carboxykinase gene (pckA) or $NADP^+$-dependent glyceraldehyde-3-phosphate dehydrogenase gene (gapB), wherein the yqzB and yqfL gene products mediate carbon catabolite repression of gluconeogenic genes. Carbon catabolite repression (CCR) is a key regulatory mechanism in bacteria controlling the expression of numerous genes involved in carbon source uptake and further metabolization in response to the availability of different carbon sources. Well-known CCR regulators in *B. subtilis* are CcpA and its co-regulators HPr and Crh, CcpB, and CcpC.

Gluconeogenic genes are involved in a central metabolic pathway, designated gluconeogenesis, in which gluconeogenic carbon sources, e.g. succinate or malate, are converted to a limited number of precursor metabolites. Examples of such precursor metabolites are glucose-6-phosphate, fructose-6-phosphate, ribose-5-phosphate, erythrose-4-phosphate, triose phosphate, 3-phosphoglycerate, and phosphoenolpyruvate. From the precursor metabolites the important building blocks for biomass production such as amino acids, nucleotides, or fatty acids are produced. The first specific step of the gluconeogenic pathway is catalyzed by phosphoenolpyruvate carboxykinase encoded by pckA which decarboxylates oxaloacetate to phosphoenolpyruvate. Another enzyme involved in gluconeogenesis in *Bacillus subtilis* and probably many other bacteria is the gapB gene product catalyzing the $NADPH/H^+$ dependent conversion of 1,3-bisphosphoglycerate to 3-phosphoglyceraldehyde. The other enzymes of the gluconeogenic pathway are shared with the corresponding enzymes of the glycolytic pathway, which is active under growth conditions with glycolytic carbon sources, like glucose, fructose, and sorbitol. PckA and gapB synthesis is subjected to CCR, i.e. pckA and gapB synthesis is very low under growth conditions with glycolytic carbon sources, but strongly derepressed during gluconeogenesis.

It has been found that both the yqzB and the yqfL genes are involved in CCR of gluconeogenic genes such as pckA and gapB.

In particular, the present invention relates to a polynucleotide comprising a DNA sequence that is selected from the group consisting of (a) a DNA sequence of a gene encoding a protein mediating carbon catabolite repression of gluconeogenic genes; (b) a DNA sequence selected from the group consisting of biologically active fragments, derivatives, variants, and orthologs of (a); (c) a DNA sequence that is substantially homologous to (a); (d) a DNA sequence encoding a polypeptide comprising the amino acid sequence represented by SEQ ID NO:2 or SEQ ID NO:4; and (e) a DNA sequence which is capable of hybridizing to the DNA sequences of (a), (b), (c) or (d) under stringent hybridizing conditions.

In one embodiment, the polynucleotide as defined above comprises the yqzB gene as represented by SEQ ID NO:1 encoding a protein as represented by SEQ ID NO:2.

In another embodiment, the polynucleotide as defined above comprises the yqfL gene as represented by SEQ ID NO:3 encoding a protein as represented by SEQ ID NO:4.

Both genes yqzB and yqfL may be part of a common operon as, e.g. in *Bacillus subtilis* or may be transcribed independently from different promoters.

The gluconeogenic genes may be any genes coding for proteins which are involved in the gluconeogenesis pathway, i.e. the conversion of gluconeogenic substrates into precursor metabolites. Examples of such genes are pckA and gapB.

As used herein, a gene encoding a protein "mediating carbon catabolite repression of gluconeogenic genes" means that said protein affects the expression of gluconeogenic genes in any direct or indirect way, such as for instance, as acting as repressor of the expression of gluconeogenic genes. The yqzB gene product mediates CCR by acting as a repressor of the expression of genes involved in gluconeogenesis, e.g. pckA and gapB.

The polynucleotides and polypeptides of the present invention are preferably provided in an isolated form, and preferably are purified to homogeneity. The term "isolated" means that the material is removed from its original environment (e.g., the natural environment if it is naturally occurring). For example, a naturally occurring polynucleotide or polypeptide present in a living organism is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

A biologically active fragment or derivative of a polypeptide means a polypeptide which retains substantially the same biological function or activity as such polypeptide of the present invention, i.e. functions as mediator of gluconeogenic genes. A biologically active fragment or derivative of a polynucleotide means a polynucleotide which encodes such a polypeptide.

"Homologous" as used herein, refers to the subunit sequence similarity between two polymeric molecules, e.g., between two nucleic acid molecules, e.g., two DNA or RNA molecules, or two polypeptide molecules. When a subunit position in both of the two molecules is occupied by the same monomeric subunit, e.g., if a position in each of two DNA molecules is occupied by adenine, then they are homologous at that position. A "best-fit" homology can be achieved by adjusting the alignment of the sequences. The homology between two sequences is a function of the number of matching or homologous positions, e.g., if half (e.g., 5 positions in a polymer 10 subunits in length), of the positions in two compound sequences are homologous then the two sequences are 50% homologous, if 90% of the positions, e.g., 9 of 10, are matched or homologous, the two sequences share 90% homology. There may be gaps of non-homologous sequences among homologous sequences. "Substantially homologous" sequences are those that differ one from the other only by conservative substitutions. For example, where the substitution is in a nucleic acid sequence, the substitution either does not cause a change in amino acid at that position, or the substitution results in a conservative amino acid substitution. A "conservative amino acid substitution" is, for example, a substitution of one amino acid for another of the same class (e.g., amino acids that share characteristics of hydrophobicity, charge, pKa, or other conformational or chemical properties, e.g., valine for leucine, arginine for lysine) or by one or more non-conservative amino acid substitutions, deletions, or insertions, located at positions of the amino acid sequence that do not destroy the biological activity of the polypeptide (as described above). An amino acid sequence is included within the scope of the invention if it differs by a modification that reduces or alters the biological activity of one domain of a multiple-domain protein, while preserving a second biological activity in a second domain of the protein.

Generally, a nucleic acid sequence is considered to be within the scope of this invention if it is at least 70%, preferably at least 75%, more preferably at least 80%, even more preferably at least 85%, even more preferably at least 90%, even more preferably at least 95%, and most preferably at least 98%, homologous to a DNA sequence encoding a protein as of the present invention, such as for instance a DNA represented by SEQ ID NO:1 or 3. A polypeptide is considered to be within the scope of this invention if it is at least 70%, preferably at least 75%, more preferably at least 80%, even more preferably at least 85%, even more preferably at least 90%, even more preferably at least 95%, and most preferably at least 98%, homologous to a polypeptide encoded by a polynucleotide sequence of the present invention, such as for instance a polypeptide represented by SEQ ID NO:2 or 4.

The present invention also encompasses polypeptides which are at least 25%, preferably at least 30%, more preferably at least 40%, even more preferably at least 50%, even more preferably at least about 60%, even more preferably at least 70%, even more preferably at least 75%, even more preferably at least 80%, even more preferably at least 85%, even more preferably at least 90%, even more preferably at least 95%, and most preferably at least 98%, identical to a polypeptide encoded by a polynucleotide sequence of the present invention, such as for instance a polypeptide represented by SEQ ID NO:2 or 4.

Two polypeptides are said to be "identical" if the sequence of amino acid residues in the two sequences is the same when aligned for maximum correspondence as described below. The terms "identical" or percent "identity", in the context of two or more polypeptide sequences, refer to two or more sequences or subsequences that are the same or have a specified percentage of amino acid residues that are the same, when compared and aligned for maximum correspondence over a comparison window, as measured using sequence comparison algorithms known in the art or by manual alignment and visual inspection.

A "comparison window", as used herein, includes reference to a segment of any one of the number of contiguous positions selected from the group consisting of from 20 to 600, usually about 50 to about 200, more usually about 100 to about 150, in which a sequence may be compared to a reference sequence of the same number of contiguous positions after the two sequences are optimally aligned.

As used herein, a variant of a polynucleotide of the present invention may be a naturally occurring allelic variant of the polynucleotide or a non-naturally occurring variant of the polynucleotide. As known in the art, an allelic variant is an alternate form of a polynucleotide sequence which may have a substitution, deletion or addition of one or more nucleotides, which does not substantially alter the function of the encoded polypeptide.

Polynucleotides corresponding to variants and homologues of the polynucleotides of the invention can be isolated based on their homology to the nucleic acids disclosed herein using the DNA sequences disclosed herein or a suitable fragment thereof, as a hybridization probe according to standard hybridization techniques preferably under stringent hybridization conditions.

Nucleic acids which hybridize under "stringent conditions" to the polynucleotide sequences identified herein and that retain the same function, i.e., mediating carbon catabolite repression of gluconeogenic genes, are within the scope of the present invention. "Stringent conditions" are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. For the purposes of this disclosure, suitable "stringent conditions" for such hybridizations are those which include hybridization in a buffer of 40% formamide, 1M NaCl, 1% sodium dodecyl sulfate (SDS) at 37° C., and at least one wash in 0.2×SSC at a temperature of at least about 50° C., usually about 55° C. to about 60° C., for 20 minutes, or equivalent conditions. A positive hybridization is at least twice above the level of background. Those of ordinary skill will readily recognize that alternative hybridization and wash conditions can be utilized to provide conditions of similar stringency, including high stringency and washing conditions.

The isolated polynucleotides as of the present invention may be obtainable from any microorganism containing an yqzB gene or a homolog or ortholog thereof, as can be found in many bacteria. Non-limiting examples of such microorganisms are selected from *Bacillus*, such as e.g. *B. subtilis, B. halodurans, Geobacillus stearothtermophilus, B. cereus, B. anthracis*, from *Staphylococcus*, such as e.g. *S. aureus, S. epidermidis*, from *Clostridium*, such as e.g. *C. difficile, C. perfringens, C. tetani*, from *Enterococcus*, such as *E. faecalis*, from *Thermoanaerobacter tengcongensis, Streptococcus agalactiae, Fusobacterium nucleatum* or *Listeria*. Preferably, the microorganism is *Bacillus*, more preferably *B. subtilis*.

The present invention further relates to a polynucleotide carrying at least one mutation as well as to a genetically engineered microorganism carrying such mutation(s), wherein said mutation leads to a relieve from carbon catabolite repression of gluconeogenic genes in said microorganism.

In one embodiment, the polynucleotide carrying the at least one mutation is derived from a polynucleotide as represented by SEQ ID NO:1 or 3 or a polynucleotide which is at least 70% homologous to SEQ ID NO:1 or 3 leading to a relieve from carbon catabolite repression of gluconeogenic genes when present in a microorganism instead of the wild type allele. Preferably, the at least one mutation is introduced into the yqzB gene.

A mutation as used herein may be any mutation leading to a non-functional polypeptide, e.g. non-functional gene products of yqzB and/or yqfL, i.e. wherein the activity of said gene products is reduced or abolished so that gluconeogenic genes are relieved from CCR. This may include for instance an alteration in the genome of a microorganism, which interferes with the synthesis of yqzB and/or yqfL or leads to the expression of a yqzB and/or yqfL encoded protein with an altered amino acid sequence whose function compared with the wild type counterpart with a non-altered amino acid sequence is completely or partially destroyed. The interference may occur at the transcriptional, translational or post-translational level.

Furthermore, a mutation may be introduced in the operator sites of the gluconeogenic genes, such as for instance pckA and gapB, whose expression is affected by the gene products of yqzB and/or yqfL. The operator site of a gene is frequently located around the promoter and the transcriptional start of the gene and serves as a binding site for a regulator protein. A mutation within the operator site would prevent binding of the regulator protein, such as YqzB, to the operator preventing the protein from having a regulatory effect on the transcription of the gene.

Furthermore, relieved from CCR of gluconeogenic genes may also be obtained by functionally linking gluconeogenic genes to constitutive promoters, which are not affected by their regulators, e.g. the gene products of yqzB and/or yqfL.

The skilled person will know how to reduce or abolish the activity of such a protein mediating CCR of gluconeogenic genes as of the present invention, preferably gene products of yqzB and/or yqfL. Such may be for instance accomplished by either genetically modifying the host organism in such a way that it produces less or no copies of said proteins mediating CCR of gluconeogenic genes, preferably gene products of yqzB and/or yqfL, than the wild type organism or by decreasing or abolishing the specific activity of said proteins mediating CCR of gluconeogenic genes, preferably gene products of yqzB and/or yqfL.

In the following description, procedures are detailed to achieve this goal, i.e. the relieve from CCR by reducing or abolishing the activity of proteins mediating CCR of gluconeogenic genes, preferably gene products of yqzB and/or yqfL.

Modifications in order to have the organism produce less or no copies of proteins mediating CCR of gluconeogenic genes, preferably gene products of yqzB and/or yqfL gene and/or genes thereof may include the use of a weak promoter, or the mutation (e.g. insertion, deletion or point mutation) of (parts of) said genes or the respective regulatory elements. Decreasing or abolishing the specific activity of such a protein may also be accomplished by methods known in the art.

Also known in the art are methods of reducing or abolishing the activity of a given protein by contacting proteins mediating CCR of gluconeogenic genes with specific inhibitors or other substances that specifically interact with proteins mediating CCR of gluconeogenic genes. In order to identify such specific inhibitors, the proteins mediating CCR of gluconeogenic genes may be expressed and tested for activity in the presence of compounds suspected to inhibit the activity of said proteins. Potential inhibiting compounds may for instance be monoclonal or polyclonal antibodies against proteins mediating CCR of gluconeogenic genes. Such antibodies may be obtained by routine immunization protocols of suitable laboratory animals.

In a further preferred embodiment, a nucleic acid of the invention as e.g. shown in SEQ ID NO:1 or 3 or the complement thereof contains at least one mutation leading to a gene product with modified function/activity. The at least one mutation may be introduced by methods described herein. In one aspect, the at least one mutation leads to a protein mediating CCR of gluconeogenic genes whose function compared to the wild type counterpart is completely or partially destroyed. Methods for introducing such mutations are well known in the art.

The term "reduction" of activity as used herein encompasses decreasing activity of one or more polypeptides in the producing organism, which in turn are encoded by the corresponding polynucleotides described herein. There are a number of methods available in the art to accomplish reduction of activity of a given protein, in this case proteins mediating CCR of gluconeogenic genes. In general, the specific activity of a protein may be decreased or the copy number of the protein may be decreased.

To facilitate such a decrease, the copy number of the genes corresponding to the polynucleotides described herein may be decreased. Alternatively, a weak promoter may be used to direct the expression of the polynucleotide. In another embodiment, the promoter, regulatory region and/or the ribosome binding site upstream of the gene can be altered to achieve the down-expression. The expression may also be reduced by decreasing the relative half-life of the messenger RNA. In another embodiment, the activity of the polypeptide itself may be decreased by employing one or more mutations in the polypeptide amino acid sequence, which decrease the activity. For example, altering the affinity of the polypeptide for its corresponding substrate may result in reduced activity. Likewise, the relative half-life of the polypeptide may be decreased. In either scenario, that being reduced gene expression or reduced activity, the reduction may be achieved by altering the composition of the cell culture media and/or methods used for culturing. "Reduced expression" or "reduced activity" as used herein means a decrease of at least 5%, 10%, 25%, 50%, 75%, or even 100%, compared to a wild-type protein, polynucleotide, gene; or the activity and/or the concentration of the protein present before the polynucleotides or polypeptides are reduced. The activity of proteins mediating CCR of gluconeogenic genes, preferably gene products of yqzB and/or yqfL, may also be reduced by contacting the protein with a specific or general inhibitor of its activity.

The alteration in the genome of the microorganism may be obtained e.g. by replacing through a single or double crossover recombination a wild type DNA sequence by a DNA sequence containing the alteration. For convenient selection of transformants of the microorganism with the alteration in its genome the alteration may, e.g. be a DNA sequence encoding an antibiotic resistance marker or a gene complementing a possible auxotrophy of the microorganism. Mutations include, but are not limited to, deletion-insertion mutations.

An alteration in the genome of the microorganism leading to a non-functional polypeptide may also be obtained by randomly mutagenizing the genome of the microorganism using e.g. chemical mutagens, radiation or transposons and selecting or screening for mutants which are able to express gluconeogenic genes under glycolytic growth conditions. For convenient selection or screening a culture of a bacterium could be mutagenized which contains in the genome a pckA promoter or a gapB promoter fused to a suitable reporter gene encoding e.g. β-galactosidase or an antibiotic resistance marker.

Expression of yqzB and/or yqfL may also be prevented or reduced by introduction of a DNA sequence complementary to the DNA sequence encoding the component at any genetic locus of the microorganism, so as to prevent or reduce the expression of the component by an antisense mechanism.

The aforementioned mutagenesis strategies for proteins mediating CCR of gluconeogenic genes, preferably yqzB and/or yqfL proteins, may result in a relieve from CCR or gluconeogenic genes such as e.g. pckA and/or gapB. This list is not meant to be limiting; variations on these mutagenesis strategies will be readily apparent to one of ordinary skill in the art. By these mechanisms, the nucleic acid and protein molecules of the invention may be utilized to generate microorganisms such as Bacillus or related strains of bacteria expressing mutated CCR mediating nucleic acid and protein molecules such that the CCR of gluconeogenic genes is relieved.

The activity of proteins mediating CCR can be measured by methods known to the person skilled in the art, such as e.g. via measuring the β-galactosidase activity of a construct containing the promoter of a gluconeogenic gene such as pckA or gapB and the β-galactosidase encoding lacZ gene. The β-galactosidase activity will increase with the decreased activity of proteins mediating CCR. Such a method is described in more detail in Example 2.

The present invention provides a genetically engineered microorganism comprising a mutated polynucleotide/polypeptide as defined above. Examples of such microorganisms may be selected from the microorganisms specified above. A preferred microorganism is a Bacillus subtilis host strain transformed with a polynucleotide carrying at least one mutation as defined above. Standard recombinant DNA techniques may be used for the construction of the polynucleotide sequence and the recombinant strains.

Transformants positive for the mutation(s), such as for instance deletion-insertion mutation(s), are selected using standard selection protocols. For example, the polynucleotide sequence used to transform the microorganism may include various selection markers, including for example antibiotic resistance markers, color producing markers, etc. Preferably, the marker is a kanamycin or a phleomycin resistance marker, and selection for the desired transformation includes identifying microorganisms capable of growing in fermentation media supplemented with kanamycin or phleomycin.

Thus, the present invention provides a Bacillus subtilis host strain relieved from CCR of gluconeogenic genes mediated by yqzB.

The present invention is furthermore directed to a polypeptide encoded by a polynucleotide as defined above. Preferably, the polypeptide is selected from an amino acid sequence as represented by SEQ ID NO:2 or 4 or homologous sequences.

In one aspect, the present invention relates to the use of a polynucleotide as defined above for the mediation of carbon catabolite repression of gluconeogenic genes.

In a further aspect of the present invention it has been surprisingly found that the relieve from carbon catabolite repression of gluconeogenic genes increases the ability of a microorganism to produce a target fermentation product.

Thus, the present invention is directed to the use of an engineered microorganisms as defined above, i.e., carrying at least one mutation, wherein said mutation leads to a relieve from carbon catabolite repression of gluconeogenic genes, for the production of a target fermentation product as well as to a process for the production of a target fermentation product.

As used herein, "target fermentation product" means any compound produced by fermentation, such as for example riboflavin, pantothenic acid, biotin, thiamin, folic acid, pyridoxine, or amino acids. A preferred target fermentation product is riboflavin.

In one aspect, the present invention provides a process for the preparation of a target fermentation product comprising cultivation of an engineered microorganism as defined above to produce such product.

Thus, the present invention is related to a process for the production of a target fermentation product comprising (a) providing a genetically engineered microorganism as defined above, (b) cultivating the microorganism of (a) under conditions that allow generation of the target fermentation product, and (c) isolation of the target fermentation product.

Cultivation means that the microorganism is inoculated into a fermentation medium supplied with all the substrates required for growth of said microorganism and production of the fermentation product. The inoculated fermentation medium is subjected to certain physico-chemical parameters, such as temperature, pH and aeration, that will allow optimal biomass growth and product accumulation. These parameters vary from type to type of microorganism to be cultivated and from compound to compound to be produced. Procedures to empirically determine these parameters are well-known to those skilled in the art and include factorial plan or composite design. To further increase fermentation product accumulation substrates required for biomass growth or product formation may be supplied to the fermentation broth during the course of the cultivation of the microorganism. For example, in the process according to the invention the microorganism may be subjected to a batch cultivation, a fed-batch cultivation with exponential and constant feeding profiles, or a cultivation in a chemostat. The process can be carried out as a continuous or semi-continuous culture or as a batch or fed-batch process in large scale industrial fermentors, varying the dilution rate from 0.3 l/l*h to 0.001 l/l*h, increasing the concentration of the components in the fermentation medium, or increasing glucose concentration up to 400 g/l.

The fermentation process may be followed by analytically determining process parameters. For example, cell dry weight (cdw) may be determined, e.g., from cell suspensions that are harvested by centrifugation, washed with distilled water, and dried at, e.g. 110° C. for 24 h to a constant weight. Concentrations of carbon dioxide and oxygen in the bioreactor feed and effluent gas may be determined with, e.g., a mass spectrometer (e.g. Prima 600, Fisons Instruments). Glucose concentrations may be determined, e.g., enzymatically with, e.g., commercial kits (e.g. Beckman). Concentrations of organic acids, acetoin, and diacyl in the culture supernatant may be determined by, e.g., HPLC on a Supelcogel C610H column (4.6×250 mm) (Sigma) with, e.g., a diode array detector (Perkin Elmer). 0.2 N phosphoric acid may be used as mobile phase at a flow rate of 0.3 ml min$^{-1}$ and 40° CC. Target fermentation product concentrations may be determined by standard methods, e.g. riboflavin concentrations may be determined as, e.g., the absorption at 440 nm ($A_{440}$) in cell-free culture broth. If $A_{440}$ exceeds 0.6, the broth may be diluted with, e.g., 0.5 M potassium phosphate buffer (pH 6.8). If $A_{440}$ exceeds 1.8, for example 0.8 ml of broth may be mixed with 0.2 ml of 0.2 M NaOH and diluted to an appropriate concentration with 0.5 M potassium phosphate buffer (pH 6.8).

The target fermentation product may be isolated from the microorganism and/or the medium. As used herein, the term "isolated" means that the target fermentation product is purified, or at least partially purified by methods including for example, filtration, centrifugation, and/or extraction. The target fermentation product may be further purified by re-crystallization from aqueous or organic solvents or applying other methods known in the art, such as for example, ion-exchange, size-exclusion, or hydrophobic interaction chromatography. For a detailed description of the procedures for isolation and purification of, e.g. riboflavin from a fermentation broth, see, e.g., EP 730034, which is incorporated herein by reference.

Suitable microorganisms as used for the production of the target fermentation product may be selected from those microorganisms defined above. Preferably the engineered microorganism, wherein the expression of gluconeogenic genes is relieved from yqzB mediated CCR, is a recombinantly produced microorganism that over-produces riboflavin.

As used herein, the term "over-produce" means that the microorganism produces the target fermentation product from a substrate that is used as a carbon source above at least 0.1% (w/w) yield, preferably above 1% (w/w) yield, such as for example, above 4% (w/w) yield.

An example of such preferred microorganism useful for the purpose of the present invention is a riboflavin producing *B. subtilis* RB50 strain, designated as RB50::[pRF69]$_n$ containing multiple (n) copies (for example about 5 to about 20 copies) of pRF69 encoding a rib operon modified with the strong phage SPO1 promoter ($P_{15}$) to enhance transcription of the rib genes. This recombinantly-produced microorganism produces significantly more riboflavin than wildtype microorganisms.

*B. subtilis* RB50 was deposited with the Agricultural Research Culture Collection (NRRL), Peoria, Ill., USA under the terms of the Budapest Treaty on May 23, 1989, and was assigned accession number B 18502. Plasmid pRF69 was deposited with the American Type Culture Collection (ATCC), Rockville, Md., USA on Jun. 6, 1990, and was assigned accession number ATCC 68338.

The present invention also includes derivatives of RB50::[pRF69]. As used herein, a "derivative" of RB50::[pRF69] is any *B. subtilis* strain which contains the engineered rib operon of pRF69 or a polynucleotide sequence that is at least 25% identical to the engineered rib operon of pRF69, preferably at least 50% identical to the engineered rib operon of pRF69, and any other genetic modification, that leads to alterations in the expression of the riboflavin biosynthetic genes. In the present invention, the percent identity of the polynucleotide sequence are determined using the BLAST program and the server at the National Center of Biotechnology Information (Bethesda, Md., USA). A "derivative" of RB50::[pRF69] may also contain alterations in the genome of RB50::[pRF69], that affect the biosynthesis of compounds that are required as precursor compounds for riboflavin biosynthesis. Furthermore, auxotrophic RB50::[pRF69] mutants are also considered "derivatives" of RB50::[pRF69]. The term auxotrophic mutant refers to a microorganism that has been modified, by e.g. a mutation, to require the addition of an exogenous compound to grow, that prior to the mutation the microorganism could produce itself.

The following examples are set forth to illustrate the processes, polynucleotides and host cells of the present invention. These examples are illustrative only and are not intended to limit the scope of the invention in any way. For example, the present invention may be varied by carrying out a fermentation process to produce a target fermentation product with any microorganism, wherein in the microorganism yqzB mediated repression of gluconeogenesis is prevented.

EXAMPLE 1

Construction of *B. subtilis* yqzB and/or yqfL Mutants Provided with gapB'-lacZ and pckA'-lacZ Reporter Fusions Standard recombinant DNA techniques were used for the construction of the polynucleotide sequences. See, for example, Sambrook et al., Molecular Cloning A Laboratory Manual (2nd Ed.) Cold Spring Harbor Laboratory Press (1989). Construction of the various *Bacillus subtilis* strains by DNA transformation or PBS1 phage transduction were done according to Harwood and Cutting, Molecular Biology Methods For *Bacillus*, John Wiley and Sons (1990).

For construction of a *Bacillus subtilis* strain GM1514 PgapB::lacZ harboring a gene fusion reporting the activity of the promoter of the gapB gene, a DNA fragment was amplified from DNA of *B. subtilis* 168 (Kunst et al. (1997) Nature 390:249-256) using primers GAPBP5 (SEQ ID NO:5) and GAPBP3 (SEQ ID NO:6) and PCR reaction conditions of 25 cycles of denaturation at 95° C. for 30 sec., annealing at 55° C. for 30 sec. and extension at 72° C. for 45 sec. The PCR product was purified using the Wizard PCR purification kit (Promega Corp.). The PCR product was ligated into the pDG1661 vector (Guérot-Fleury et al. (1996) Gene 180:57-61), resulting in plasmid pSF114. Plasmid pSF114 was transformed into *B. subtilis* wild type strain 168 and selected on LB plates containing chloramphenicol to a final concentration of 5 mg×L$^{-1}$. One transformant clone, checked for amylase minus phenotype and sensitivity to spectinomycin, was renamed GM1514.

For construction of a *Bacillus subtilis* strain PS1649 PpckA::lacZ harboring a gene fusion reporting the activity of the promoter of the pckA gene, a DNA fragment was amplified from DNA of *B. subtilis* 168 using primers PCKAP5 (SEQ ID NO:7) and PCKAP3 (SEQ ID NO:8) and the same PCR reaction conditions as above. The PCR product was purified using the Wizard PCR purification kit (Promega Corp.). The PCR product was ligated into the pDG1661 vector (Guérot-Fleury et al. (1996) Gene 180:57-61), resulting in plasmid pPS19. Plasmid pPS19 was transformed into *B. subtilis* wild type strain 168 and selected on LB plates containing chloramphenicol to a final concentration of 5 mg×L$^{-1}$. One transformant clone, checked for amylase minus phenotype and sensitivity to spectinomycin, was renamed PS1649.

For construction of *Bacillus subtilis* strain PS1722 PgapB::lacZ ΔyqzB, a DNA fragment was amplified from DNA of *B. subtilis* microorganism 168 using primers YQZBUP5 (SEQ ID NO:9) and YQZBUP3 (SEQ ID NO:10) and the same PCR reaction conditions as above. In a further PCR reaction, another DNA fragment was amplified from DNA of *B. subtilis* microorganism 168 using primers YQZBDOWN5 (SEQ ID NO:11) and YQZBDOWN3 (SEQ ID NO:12) and the same PCR reaction conditions as above. The PCR products were purified using the Wizard PCR purification kit (Promega Corp.), ligated together and further ligated into the pRN5101 vector (Poncet et al. (1997) Appl. Environ. Microbiol. 63:4413-4420), resulting in plasmid pPS65. Plasmid pPS65 was transformed into *B. subtilis* strain GM1514 and selected at 42° C. on LB plates containing erythromycin to a final concentration of 0.5 mg×L$^{-1}$. Transformants were then streaken on LB plates at 28° C. Several clones were tested on glucose minimal medium plates for β-galactosidase activity and on LB erythromycin plates for growth. A β-galactosidase positive and erythromycin sensitive clone was renamed PS1722.

For construction of *Bacillus subtilis* strain PS1633 PgapB::lacZ ΔyqfL, a DNA fragment was amplified from DNA of *B. subtilis* microorganism 168 using primers YQFLUP5 (SEQ ID NO:13) and YQFLUP3 (SEQ ID NO:14) and PCR reaction conditions as above. Another DNA fragment was amplified from DNA of *B. subtilis* microorganism 168 using primers YQFLDOWN5 (SEQ ID NO:15) and YQFLDOWN3 (SEQ ID NO:16) and same PCR reaction conditions as above. The PCR products were purified using the Wizard PCR purification kit (Promega Corp.), ligated with the XbaI-BamHI DNA fragment carrying the phleomycin resistance gene of pIC22 (Steinmetz and Richter (1994) Gene 142:79-83) and then ligated into the pJH101 plasmid vector (Ferrari et al. (1983) J. Bacteriol. 154:1513-1515), resulting in plasmid pPS13. The plasmid pPS13 was then transformed into *B. subtilis* strain GM1514 and selected on LB plates containing phleomycin to a final concentration of 0.25 mg×L$^{-1}$ to give *B. subtilis* microorganism PS1633.

For construction of *Bacillus subtilis* strain PS1723 PgapB::lacZ ΔyqzB-yqfL, a DNA fragment was amplified from DNA of *B. subtilis* microorganism 168 using primers 5YQZBE (SEQ ID NO:17) and ATGYQZBX (SEQ ID NO:18) and PCR reaction conditions as described above. The PCR product was purified using the Wizard PCR purification kit (Promega Corp.) and ligated with plasmid pPS13 linearized with XbaI and EagI, resulting in plasmid pPS30. The plasmid pPS30 was then transformed into *B. subtilis* strain GM1514 and selected on LB plates containing phleomycin to a final concentration of 0.25 mg×L$^{-1}$ to give *B. subtilis* microorganism PS1723.

For construction of *Bacillus subtilis* strain PS1621 yqzB::pEC23, a DNA fragment is amplified from DNA of *B. subtilis* microorganism 168 using primers 5YQZBMUT (SEQ ID NO:19) and 3YQZBMUT (SEQ ID NO:20) and PCR reaction conditions as above. The PCR product is purified using the Wizard PCR purification kit (Promega Corp.) and ligated into the pMUTIN2 vector (Vagner et al. (1998) Microbiology 144:3097-3104), resulting in plasmid pMUTYQZB. The plasmid pMUTYQZB is transformed into *B. subtilis* microorganism 168 and selected on LB plates containing erythromycin to a final concentration of 0.5 mg×L$^{-1}$ to give *B. subtilis* microorganism SA1620. In vivo replacement in the genome of SA1620 by homologous recombination of a kanamycin resistance cassette for lacZ and the erythromycin resistance gene is obtained using pEC23 (Doan and Aymerich (2003) Molecular Microbiology 47:1709-1721). Plasmid pEC23 is a pBR322 derivative containing a chloramphenicol resistance cassette and, between a DNA fragment corresponding to the 5'-end of the lacZ gene and a fragment corresponding to the 3'-end of the erythromycin gene of pMUTIN2, a kanamycin resistance cassette. One of the resulting kanamycin (10 mg×L$^{-1}$) resistant and chloramphenicol and erythromycin sensitive transformants obtained upon transformation of SA1620 with pEC23 is selected and renamed PS1621.

For construction of *Bacillus subtilis* strain PS1650 PpckA::lacZ yqzB::pEC23, total DNA purified from *B. subtilis* strain PS1621 is transformed into *B. subtilis* strain PS1649 and selected on LB plates containing kanamycin to a final concentration of 10 mg×L$^{-1}$ to give PS1650.

For construction of *Bacillus subtilis* strain PS1651 PpckA::lacZ ΔyqfL, total DNA purified from *B. subtilis* strain PS1633 was transformed into *B. subtilis* strain PS1649 and selected on LB plates containing phleomycin to a final concentration of 0.25 mg×L$^{-1}$ to give *B. subtilis* microorganism PS1651.

EXAMPLE 2

Expression of gap-lacZ and pckA-lacZ Reporter Fusions in Various *B. subtilis* Mutants Cultivated with Glycolytic or Gluconeogenic Carbon Sources Relieve from yqzB mediated CCR of gluconeogenic genes can be achieved by preventing or reducing the expression of the yqzB gene. This is shown in this example by comparing the β-galactosidase activity in *B. subtilis* strains containing a wild type or a deleted yqzB gene and provided with a reporter fusion of the gapB or the pckA promoter with the β-galactosidase encoding lacZ gene. Promoter/lacZ fusions are frequently used to demonstrate the regulatory activity of transcriptional repressors or activators on the expression of their target genes (Guérout-Fleury et al. (1996) Gene 180:57-61).

The *B. subtilis* mutant strains obtained according to Example 1 were cultivated in CQTHC medium (C mineral medium [70 mM K$_2$HPO$_4$, 30 mM KH$_2$PO$_4$, 25 mM (NH$_4$)$_2$SO$_4$, 0.5 mM MgSO$_4$, 0.01 mM MnSO$_4$, 22 mg of ferric ammonium citrate per liter] supplemented with tryptophan 0.005% (w/v), glutamine 0.15% (w/v) and casein hydrolysate 0.05% (w/v)) with glucose (10 g/l) as glycolytic and succinate (10 g/l) plus glutamate (10 g/l) as gluconeogenic carbon sources. Exponentially growing bacteria were harvested by centrifugation. The β-galactosidase activity was measured using the method of Miller (Miller (1972) Experiments in Molecular Genetics. Cold Spring Harbor, N.Y.: Cold Spring Harbor Laboratory Press) with extracts of the harvested bacteria prepared by lysozyme treatment and centrifugation. The results are shown in Table 1. Expression of β-galactosidase activity in the strains GM1514 provided with the gapB-lacZ reporter fusion and PS1649 provided with pckA-lacZ reporter fusions was 70-fold and 34-fold, respectively, increased if gluconeogenic cultivation conditions were applied compared to cultivation conditions with glucose as glycolytic carbon source. The result indicates that the expression of the gluconeogenic genes gapB and pckA is subjected to CCR. In the yqzB deletion mutants PS1722 and PS1650 expression of β-galactosidase activity was further increased and reached a level that was about 5-fold above the level determined in the yqzB wild type strains cultivated with gluconeogenic carbon sources. In the yqzB deletion mutants expression of β-galactosidase activity was hardly affected by the carbon source in the cultivation medium. Obviously, even under gluconeogenic cultivation conditions, yqzB mediated CCR on gluconeogenesis was only partly prevented. Complete relieve from yqzB mediated repression could be achieved upon deletion of the gene. Expression of β-galactosidase activity in the yqfL deletion mutants PS1633 and PS1651 under gluconeogenic cultivation conditions was significantly reduced compared to the corresponding wild type strains PS1514 and PS1649. However, similar β-galactosidase activities were found in the yqzB-yqfL double mutant PS1723 and in PS1722 carrying only the yqzB mutation. These results indicate that the yqzB deletion is epistatic to a yqfL mutation and suggest that the yqfL gene product interferes with the inhibitory activity of the yqzB gene product.

TABLE 1

Expression of lacZ reporter fusions in various *B. subtilis* mutants.

| Strain and relevant genotype | β-galactosidase activity | |
|---|---|---|
| | glucose | succinate/glutamate |
| GM1514 (PgapB::lacZ) | 20 | 1407 |
| PS1722 (PgapB::lacZ ΔyqzB) | 5577 | 6605 |
| PS1633 (PgapB::lacZ ΔyqfL) | 7 | 456 |
| PS1723 (PgapB::lacZ Δ (yqzB-yqfL) | 5644 | 6369 |
| PS1649 (PpckA::lacZ) | 77 | 2571 |
| PS1650 (PpckA::lacZ yqzB'::pEC23) | 12783 | 13792 |
| PS1651 (PpckA::lacZ ΔyqfL) | 34 | 659 |

EXAMPLE 3

Construction of a yqzB Deletion Mutant of *B. subtilis* RB50::pRF69

*B. subtilis* microorganism PS1621 of Example 1 is used as a donor microorganism for preparation of a PBS1 phage lysate. This lysate is used to transduce the riboflavin production microorganism RB50 provided with the modified riboflavin operon pRF69. RB50 refers to the host microorganism of *B. subtilis*, which contains several mutations introduced to improve production of nucleotides and riboflavin. Plasmid pRF69 refers to a rib operon modified by the introduction of strong phage promoters which is introduced at the rib locus of pRF50. A detailed description of the microorganism RB50 and the modified rib operon pRF69 is presented EP 405370. One of the kanamycin-resistant colonies resulting from the transduction of *Bacillus subtilis* RB50::pRF69 with the PS1621 derived PBS1 lysate is confirmed by standard PCR to contain the disrupted yqzB gene and is renamed RB50::[pRF69] ΔyqzB.

EXAMPLE 4

Cultivation of RB50::[pRF69] ΔyqzB and the Parent Strain RB50::[pRF69]

For preparation of seed cultures, frozen RB50::[pRF69] or RB50::[pRF69] ΔyqzB cultures are thawed and 3 µl of the cultures are inoculated into 1 ml VY medium (VY medium: 25 g/l of Difco veal infusion plus 5 g/l yeast extract plus 15 g/l glucose). The cultures are incubated at 37° C. for about 10 h until turbidity changes visibly. From the VY cultures 10 µl are removed to inoculate 1 ml cultures of minimal medium M9 (per liter of ddH$_2$O: 12.8 g Na$_2$HPO$_4$.7H$_2$O, 3.0 g KH$_2$PO$_4$, 0.5 g NaCl, 1.0 g NH$_4$Cl, 1 ml 1M MgSO$_4$, 1 ml 0.1M CaCl$_2$, 125.0 mg MgCl$_2$.6H$_2$O, 5.5 mg CaCl$_2$, 13.5 mg FeCl$_2$.6H$_2$O, 1.0 mg MnCl$_2$.4H$_2$O, 1.7 mg ZnCl$_2$, 0.43 mg CuCl$_2$.2H$_2$O, 0.6 mg CoCl$_2$.6H$_2$O, 0.6 mg Na$_2$MoO$_4$.2H$_2$O) supplemented with either 5 g/l glucose, 5 g/l raffinose or 5 g/l malate. Cultivations are done overnight at 37° C. The main batch cultivations are initiated by inoculation of 10 µl of the overnight cultures into 1 ml of M9 supplemented with 5 g/l of the appropriate carbon source. In case raffinose is used as carbon source 0.5 g/l yeast extract are added to the culture. Each cultivation condition is done in triplicate at 37° C. for 30 hours in a deep well plate. To measure the riboflavin concentration the culture broth are centrifuged for 10 min at 5,000 rpm at 4° C. The supernatants are diluted with NaOH and the absorption at 440 nm ($A_{440}$) is determined immediately. The dilutions are adjusted to achieve readings between 0.1 and 1.0 absorption units. The riboflavin concentration is calculated by comparing the absorption of the samples to those of a riboflavin standard (Sigma, St. Luis, Mo., USA). As shown in Table 2, strain RB50::[pRF69] containing a yqzB insertion mutation is superior with regard to riboflavin production compared to the parent strain RB50::[pRF69] carrying a wild type yqzB gene. The increase in the riboflavin titer is observed with all of the 3 carbon sources applied.

TABLE 2

Riboflavin titer in cultures of RB50::[pRF69] ΔyqzB and the parent strain RB50::[pRF69].

| | Riboflavin [mg/ml] | | |
|---|---|---|---|
| | M9 + 0.5% glucose | M9 + 0.5% raffinose + 0.05% yeast extract | M9 + 0.5% malate |
| *B. subtilis* RB50::[pRF69] | 79.9 ± 1.3 | 124.3 ± 9.1 | 24.0 ± 3.3 |
| *B. subtilis* RB50::[pRF69] ΔyqzB | 108.9 ± 4.3 | 235.4 ± 28.8 | 32.5 ± 3.7 |

The invention claimed is:

1. A process for preparing riboflavin, said process comprising:
   (a) cultivating a genetically engineered *Bacillus* microorganism under conditions that allow production of riboflavin; and
   (b) isolating the riboflavin;
   wherein the genetically engineered *Bacillus* microorganism has a disrupted yqzB gene and transcription repressor function of the polypeptide encoded by the disrupted yqzB gene is reduced as compared with transcription repressor function of a polypeptide encoded by a corresponding wild type yqzB gene.

2. The process according to claim 1, wherein the genetically engineered *Bacillus* microorganism is *Bacillus subtilis*.

3. The process according to claim 1, wherein the genetically engineered *Bacillus* microorganism is *Bacillus subtilis* RB50::[pRF69].

4. The process according to claim 1, wherein carbon catabolite repression of pckA gene expression or carbon catabolite repression of gapB gene expression is relieved in the genetically engineered *Bacillus* microorganism.

5. The process according to claim 1, wherein the corresponding wild type yazB gene comprises the nucleotide sequence of SEQ ID NO: 1.

6. The process according to claim 1, wherein the corresponding wild type yqzB gene encodes a polypeptide comprising the amino acid sequence of SEQ ID NO:2.

* * * * *

SEQUENCE LISTING

```
<160> NUMBER OF SEQ ID NOS: 20

<210> SEQ ID NO 1
<211> LENGTH: 636
<212> TYPE: DNA
<213> ORGANISM: Bacillus subtilis

<400> SEQUENCE: 1
atgagtacga tcgaactaaa taaacggcaa gaacatattt tgcagattgt aaaagaaaac      60
gggccgatta caggggagca tattgcagaa aagctgaacc taaccagggc gacattgcgc     120
ccggatttag ccatactcac catgtcagga ttcctcgagg cgcgcccgag agtcggttat     180
ttctatacgg gaaaaaccgg cacacagctt tggcggata aactcaaaaa gcttcaggtg     240
aaagactttc aatctatccc cgtagtgatt cacgaaaacg tttctgtgta cgatgcgatt     300
tgcaccatgt ttttagaaga tgtaggtact ctgtttgtgg tggaccgcga tgctgtttta     360
```

```
gtcggggtgc tttcacgaaa agacttgctc agagcgagca ttggccagca ggagcttaca    420
tcggtccctg ttcacatcat catgacaagg atgccgaaca ttacggtgtg cagacgcgag    480
gattatgtga tggacattgc aaagcactta atagaaaaac aaattgatgc actgcctgtc    540
atcaaagaca ccgataaagg ctttgaagtg atcggcagag tgacaaaaac aaatatgacc    600
aaaatacttg tcagtttatc tgaaaatgaa atccta                              636
```

<210> SEQ ID NO 2
<211> LENGTH: 212
<212> TYPE: PRT
<213> ORGANISM: Bacillus subtilis

<400> SEQUENCE: 2

```
Met Ser Thr Ile Glu Leu Asn Lys Arg Gln Glu His Ile Leu Gln Ile
1               5                   10                  15

Val Lys Glu Asn Gly Pro Ile Thr Gly Glu His Ile Ala Glu Lys Leu
            20                  25                  30

Asn Leu Thr Arg Ala Thr Leu Arg Pro Asp Leu Ala Ile Leu Thr Met
        35                  40                  45

Ser Gly Phe Leu Glu Ala Arg Pro Arg Val Gly Tyr Phe Tyr Thr Gly
    50                  55                  60

Lys Thr Gly Thr Gln Leu Leu Ala Asp Lys Leu Lys Leu Gln Val
65                  70                  75                  80

Lys Asp Phe Gln Ser Ile Pro Val Val Ile His Glu Asn Val Ser Val
                85                  90                  95

Tyr Asp Ala Ile Cys Thr Met Phe Leu Glu Asp Val Gly Thr Leu Phe
            100                 105                 110

Val Val Asp Arg Asp Ala Val Leu Val Gly Val Leu Ser Arg Lys Asp
        115                 120                 125

Leu Leu Arg Ala Ser Ile Gly Gln Gln Glu Leu Thr Ser Val Pro Val
    130                 135                 140

His Ile Ile Met Thr Arg Met Pro Asn Ile Thr Val Cys Arg Arg Glu
145                 150                 155                 160

Asp Tyr Val Met Asp Ile Ala Lys His Leu Ile Glu Lys Gln Ile Asp
                165                 170                 175

Ala Leu Pro Val Ile Lys Asp Thr Asp Lys Gly Phe Glu Val Ile Gly
            180                 185                 190

Arg Val Thr Lys Thr Asn Met Thr Lys Ile Leu Val Ser Leu Ser Glu
        195                 200                 205

Asn Glu Ile Leu
    210
```

<210> SEQ ID NO 3
<211> LENGTH: 810
<212> TYPE: DNA
<213> ORGANISM: Bacillus subtilis

<400> SEQUENCE: 3

```
atgaataacc gcatcatcta tgttgtatcg gattccgtcg gtgaaacggc tgaattggta    60
gtaaaagcag cactcagcca atttaacgga tcggcggatg atactcatgt aagaagaatt    120
ccttatgttg aagatatagg cactatcaat gaagtgattt cacttgcaaa ggcagacggc    180
ggcattatct gttttacact cgtggtgccg gaaatcagag aatatttgat agccgaagcg    240
gaaaaagcaa atgttttata ttatgatatt atcggcccgt tgattgataa aatggaaaca    300
gcctacggtt aacagcgaaa atacgaaccg ggcggggtgc gccagcttga tgaagattat    360
```

-continued

```
ttcaaaaaag tggaggccat cgagtttgca gttaaatacg atgatggacg tgatccaaga    420
gggattttaa aagctgatat cgttttgatc ggcgtgtcaa gaacgtctaa acaccgctg     480 tctcaatatc tcgcacacaa acgcctgaag gttgccaatg ttccgattgt accggaggtt   540
gatccgccgg aagaactctt taacgttgat ccgaaaaaat gcatcggttt aaagattagc   600
cctgataaac tgaatcatat cagaaaagaa cgtttaaaat cactcgggct taatgataaa   660 gcgattatg  caaatatcaa cagaatcaaa gaggaactcg agtatttcga aaagattgtg   720
gatcggatcg gctgccaggt tgttgatgtt tcaaataaag cggttgagga acagcaaat    780 attatccatc atctcaaaac aaaaaacata                                      810
```

<210> SEQ ID NO 4
<211> LENGTH: 270
<212> TYPE: PRT
<213> ORGANISM: Bacillus subtilis

<400> SEQUENCE: 4

```
Met Asn Asn Arg Ile Ile Tyr Val Val Ser Asp Ser Val Gly Glu Thr
1               5                   10                  15

Ala Glu Leu Val Val Lys Ala Ala Leu Ser Gln Phe Asn Gly Ser Ala
            20                  25                  30

Asp Asp Thr His Val Arg Arg Ile Pro Tyr Val Glu Asp Ile Gly Thr
        35                  40                  45

Ile Asn Glu Val Ile Ser Leu Ala Lys Ala Asp Gly Gly Ile Ile Cys
    50                  55                  60

Phe Thr Leu Val Val Pro Glu Ile Arg Glu Tyr Leu Ile Ala Glu Ala
65                  70                  75                  80

Glu Lys Ala Asn Val Leu Tyr Tyr Asp Ile Ile Gly Pro Leu Ile Asp
                85                  90                  95

Lys Met Glu Thr Ala Tyr Gly Leu Thr Ala Lys Tyr Glu Pro Gly Arg
            100                 105                 110

Val Arg Gln Leu Asp Glu Asp Tyr Phe Lys Lys Val Glu Ala Ile Glu
        115                 120                 125

Phe Ala Val Lys Tyr Asp Asp Gly Arg Asp Pro Arg Gly Ile Leu Lys
    130                 135                 140

Ala Asp Ile Val Leu Ile Gly Val Ser Arg Thr Ser Lys Thr Pro Leu
145                 150                 155                 160

Ser Gln Tyr Leu Ala His Lys Arg Leu Lys Val Ala Asn Val Pro Ile
                165                 170                 175

Val Pro Glu Val Asp Pro Pro Glu Glu Leu Phe Asn Val Asp Pro Lys
            180                 185                 190

Lys Cys Ile Gly Leu Lys Ile Ser Pro Asp Lys Leu Asn His Ile Arg
        195                 200                 205

Lys Glu Arg Leu Lys Ser Leu Gly Leu Asn Asp Lys Ala Ile Tyr Ala
    210                 215                 220

Asn Ile Asn Arg Ile Lys Glu Glu Leu Glu Tyr Phe Glu Lys Ile Val
225                 230                 235                 240

Asp Arg Ile Gly Cys Gln Val Val Asp Val Ser Asn Lys Ala Val Glu
                245                 250                 255

Glu Thr Ala Asn Ile Ile His His Leu Lys Thr Lys Asn Ile
            260                 265                 270
```

<210> SEQ ID NO 5
<211> LENGTH: 24
<212> TYPE: DNA

```
<213> ORGANISM: Artificial Sequence
<220> FEATURE:
<223> OTHER INFORMATION: PCR primer

<400> SEQUENCE: 5
ggaattctgc ttggggagcg aatc                                            24

<210> SEQ ID NO 6
<211> LENGTH: 27
<212> TYPE: DNA
<213> ORGANISM: Artificial Sequence
<220> FEATURE:
<223> OTHER INFORMATION: PCR primer

<400> SEQUENCE: 6
gccgaagctt catgttggac acccctt                                         27

<210> SEQ ID NO 7
<211> LENGTH: 30
<212> TYPE: DNA
<213> ORGANISM: Artificial Sequence
<220> FEATURE:
<223> OTHER INFORMATION: PCR primer

<400> SEQUENCE: 7
ttagaattca tacaaccttg caacaggtta                                      30

<210> SEQ ID NO 8
<211> LENGTH: 31
<212> TYPE: DNA
<213> ORGANISM: Artificial Sequence
<220> FEATURE:
<223> OTHER INFORMATION: PCR primer

<400> SEQUENCE: 8
attggatcca tatgaaacct tcctttatcg t                                    31

<210> SEQ ID NO 9
<211> LENGTH: 29
<212> TYPE: DNA
<213> ORGANISM: Artificial Sequence
<220> FEATURE:
<223> OTHER INFORMATION: PCR primer

<400> SEQUENCE: 9
cgcggatccg tactctgcgc tgcataaag                                       29

<210> SEQ ID NO 10
<211> LENGTH: 32
<212> TYPE: DNA
<213> ORGANISM: Artificial Sequence
<220> FEATURE:
<223> OTHER INFORMATION: PCR primer

<400> SEQUENCE: 10
aatctagaac tcaccacctt ttcacttcat ag                                   32

<210> SEQ ID NO 11
<211> LENGTH: 33
<212> TYPE: DNA
<213> ORGANISM: Artificial Sequence
<220> FEATURE:
<223> OTHER INFORMATION: PCR primer

<400> SEQUENCE: 11
aatctagaat cctataagat tgcaaactaa cgg                                  33
```

```
<210> SEQ ID NO 12
<211> LENGTH: 33
<212> TYPE: DNA
<213> ORGANISM: Artificial Sequence
<220> FEATURE:
<223> OTHER INFORMATION: PCR primer

<400> SEQUENCE: 12
accaagcttg agacagcggt gttttagacg ttc                                33

<210> SEQ ID NO 13
<211> LENGTH: 28
<212> TYPE: DNA
<213> ORGANISM: Artificial Sequence
<220> FEATURE:
<223> OTHER INFORMATION: PCR primer

<400> SEQUENCE: 13
attaagcttc ctcgaggcgc gcccgaga                                      28

<210> SEQ ID NO 14
<211> LENGTH: 29
<212> TYPE: DNA
<213> ORGANISM: Artificial Sequence
<220> FEATURE:
<223> OTHER INFORMATION: PCR primer

<400> SEQUENCE: 14
atatctagat tatcccccg ttagtttgc                                      29

<210> SEQ ID NO 15
<211> LENGTH: 29
<212> TYPE: DNA
<213> ORGANISM: Artificial Sequence
<220> FEATURE:
<223> OTHER INFORMATION: PCR primer

<400> SEQUENCE: 15
attggatcct caggacgctc tatcctggg                                     29

<210> SEQ ID NO 16
<211> LENGTH: 28
<212> TYPE: DNA
<213> ORGANISM: Artificial Sequence
<220> FEATURE:
<223> OTHER INFORMATION: PCR primer

<400> SEQUENCE: 16
agtgaattca caacaatatc tcccggtt                                      28

<210> SEQ ID NO 17
<211> LENGTH: 22
<212> TYPE: DNA
<213> ORGANISM: Artificial Sequence
<220> FEATURE:
<223> OTHER INFORMATION: PCR primer

<400> SEQUENCE: 17
ttttcggccg tactctgcgc tg                                            22

<210> SEQ ID NO 18
<211> LENGTH: 26
<212> TYPE: DNA
<213> ORGANISM: Artificial Sequence
<220> FEATURE:
<223> OTHER INFORMATION: PCR primer
```

```
<400> SEQUENCE: 18
gctctagatc gtactcacca cctttt                                              26

<210> SEQ ID NO 19
<211> LENGTH: 27
<212> TYPE: DNA
<213> ORGANISM: Artificial Sequence
<220> FEATURE:
<223> OTHER INFORMATION: PCR primer

<400> SEQUENCE: 19
agtgaattca gaaaacgggc cgattac                                             27

<210> SEQ ID NO 20
<211> LENGTH: 27
<212> TYPE: DNA
<213> ORGANISM: Artificial Sequence
<220> FEATURE:
<223> OTHER INFORMATION: PCR primer

<400> SEQUENCE: 20
attggatcca aatcgcatcg tacacag                                             27
```